(12) United States Patent
Koulikov

(10) Patent No.: US 9,581,492 B2
(45) Date of Patent: *Feb. 28, 2017

(54) SYSTEMS AND METHODS FOR CONTROLLING THE OPTICAL PATH LENGTH BETWEEN A LASER AND AN OPTICAL CAVITY

(71) Applicant: LI-COR, Inc., Lincoln, NE (US)

(72) Inventor: Serguei Koulikov, Los Altos, CA (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/823,767

(22) Filed: Aug. 11, 2015

(65) Prior Publication Data
US 2016/0041031 A1    Feb. 11, 2016

Related U.S. Application Data

(63) Continuation of application No. 14/052,618, filed on Oct. 11, 2013, now Pat. No. 9,116,047.

(51) Int. Cl.
  *G01J 3/02* (2006.01)
  *G01J 3/42* (2006.01)
  *G01J 3/45* (2006.01)
  *G01N 21/41* (2006.01)
  *G01N 21/39* (2006.01)

(52) U.S. Cl.
  CPC ............... *G01J 3/027* (2013.01); *G01J 3/42* (2013.01); *G01J 3/45* (2013.01); *G01N 21/41* (2013.01); *G01N 2021/391* (2013.01); *G01N 2021/399* (2013.01)

(58) Field of Classification Search
  CPC .... G01J 3/45; G01J 3/027; G01J 3/42; G01N 21/41; G01N 2021/399
  USPC ...... 356/432–444, 469, 502; 372/12, 20, 26, 372/32, 92, 98
  See application file for complete search history.

(56) References Cited

U.S. PATENT DOCUMENTS

| 3,869,210 A | 3/1975 | Fletcher et al. |
| 4,011,013 A | 3/1977 | Barrett |
| 4,733,397 A | 3/1988 | Gallagher et al. |
| 4,958,921 A | 9/1990 | Early |

(Continued)

FOREIGN PATENT DOCUMENTS

WO    WO 2011/109557 A1    9/2011

OTHER PUBLICATIONS

Owens, James C., "Optical Refractive Index of Air: Dependence on Pressure, Temperature and Composition," Applied Optics, Jan. 1967, vol. 6, No. 1, pp. 51-59.

(Continued)

*Primary Examiner* — Sang Nguyen
(74) *Attorney, Agent, or Firm* — Leydig, Voit & Mayer, LTD; Gerald T. Gray

(57) ABSTRACT

Systems and methods for controlling the optical path length between a feedback enabled laser and a cavity, and hence the optical feedback phase. A phasor element, positioned along an optical path between the laser and the cavity coupling mirror, includes a gas medium within a volume defined by the phasor element. The phasor element is configured to adjust or control an optical path length of the laser light between the laser and the cavity coupling mirror by adjusting or controlling a density of the gas medium within the phasor volume.

20 Claims, 7 Drawing Sheets

(56) References Cited

U.S. PATENT DOCUMENTS

| | | | |
|---|---|---|---|
| 5,260,663 A | 11/1993 | Blades | |
| 5,313,270 A | 5/1994 | Fishman et al. | |
| 5,452,084 A | 9/1995 | Mitchell et al. | |
| 5,621,744 A | 4/1997 | Kikuchi et al. | |
| 5,790,259 A | 8/1998 | Mizuhata et al. | |
| 5,999,547 A | 12/1999 | Schneider et al. | |
| 6,205,159 B1 | 3/2001 | Sesko et al. | |
| 6,323,481 B2 | 11/2001 | Ueki | |
| 6,421,130 B1 | 7/2002 | Phillion | |
| 6,455,829 B1 | 9/2002 | Fukumura | |
| 7,098,441 B2 | 8/2006 | Yamaguchi et al. | |
| 7,450,240 B2 | 11/2008 | Morville et al. | |
| 7,639,373 B2 | 12/2009 | Torii et al. | |
| 8,659,758 B2* | 2/2014 | Koulikov | G01N 21/3504 356/436 |
| 8,659,759 B2* | 2/2014 | Koulikov | G01J 3/021 356/213 |
| 8,675,209 B2 | 3/2014 | Usami | |
| 9,116,047 B2* | 8/2015 | Koulikov | G01J 3/45 |
| 2002/0097402 A1 | 7/2002 | Manning | |
| 2002/0134909 A1 | 9/2002 | Shiota et al. | |
| 2003/0043377 A1 | 3/2003 | Balobeck | |
| 2008/0111993 A1 | 5/2008 | Miller | |
| 2010/0002234 A1 | 1/2010 | Cormier et al. | |
| 2011/0214479 A1 | 9/2011 | Kachanov et al. | |
| 2012/0154807 A1 | 6/2012 | Usami | |
| 2013/0050706 A1* | 2/2013 | Koulikov | G01J 3/021 356/437 |
| 2013/0083328 A1* | 4/2013 | Koulikov | G01N 21/3504 356/469 |
| 2013/0100973 A1 | 4/2013 | Bondu et al. | |

OTHER PUBLICATIONS

Rentschler, Harvey Clayton, "A New Method for Measuring the Index of Refraction of a Gas for Different Light-waves and Results Obtained for Several Gases," The Astrophysical Journal, Dec. 1908, vol. 28, No. 5, pp. 345-359.

Zucker, Michael E. et al., "Measurement of Optical Path Fluctuations due to Residual Gas in the LIGO 40 Meter Interferometer," Proceedings of the Seventh Marcel Grossman Meeting on recent developments in theoretical and experimental general relativity, gravitation, and relativistic field theories. Proceedings of the Meeting held at Stanford University, Jul. 24-30, 1994. Edited by Robert T. Jantzen, G. Mac Keiser, and Remo Ruffini, River Edge, New Jersey: World Scientific, 1996., p. 1434.

Index of Refraction (n) of Air, pp. 1-4.

European Patent Office, International Search Report and the Written Opinion in International Patent Application No. PCT/US2014/059966 (Jan. 27, 2015).

* cited by examiner

SYSTEMS AND METHODS FOR CONTROLLING THE OPTICAL PATH LENGTH BETWEEN A LASER AND AN OPTICAL CAVITY

CROSS-REFERENCE TO RELATED APPLICATIONS

This patent application is a continuation application of U.S. patent application Ser. No. 14/052,618, filed Oct. 11, 2013, which is incorporated herein by reference for all purposes.

BACKGROUND

The present invention relates generally to optical spectroscopy systems and methods and more specifically to systems and methods for controlling the optical path length between a laser and cavity in optical spectroscopy systems.

In cavity enhanced optical absorption spectroscopy systems and methods, radiation of a laser is directed into a resonance cavity, and the optical intensity inside the cavity is observed. The optical frequency of the laser can be periodically scanned. If it is assumed for clarity that the laser linewidth is much smaller than the cavity resonance width, at the moment when the laser light frequency coincides with a cavity mode transmission peak the optical intensity inside the resonance cavity reflects total cavity loss, and the total cavity loss can be quantitatively determined provided that the incident intensity and cavity parameters are known. The total cavity loss is a sum of the cavity mirror losses and losses caused by absorption of a gas mixture present in the cavity. The lower the cavity mirror losses, or equivalently, the higher each mirror's reflectivity—the smaller the absorption of the intra-cavity gas mixture that can be detected. With very high reflectivity mirrors, the laser linewidth will become too large compared to the cavity resonance width, thus limiting achievable enhancement of the gas mixture absorption by the cavity. This can be helped by narrowing the laser linewidth using optical feedback from the cavity and a laser that is sensitive or responsive to optical feedback from the cavity. With such a laser during the scan, as the frequency of the laser light approaches the frequency of one of the cavity modes, the laser locks to that mode. By saying that the laser is locked to the mode it is meant that the laser linewidth becomes much smaller than the resonance mode width, and that regardless whether the frequency scan range of the unlocked laser may be large, in a locked condition the optical frequency of the laser will change only within the resonance peak. As the laser frequency scan continues, the laser will lose the lock to the current cavity mode and relock to the next cavity mode that it approaches. Due to the optical feedback effect, the laser optical frequency during the scan will essentially take a number of discrete values corresponding to the peaks of the cavity mode resonances that are equidistant in optical frequency. A discrete absorption spectrum of the analyzed gas can thus be obtained by sequential coupling to the entire set of the cavity modes within the scan range, and the trace gas concentration can be derived from the absorption spectrum. This sub-family of cavity enhanced optical absorption spectroscopy systems and methods that uses optical feedback will be referred to as optical feedback cavity enhanced absorption spectroscopy (OF CEAS). For simplicity, optical feedback assisted cavity ring-down spectroscopy is included in the OF CEAS definition.

In OF CEAS, the strength of the optical feedback from the resonance cavity to the laser has to be within certain limits, otherwise it is impossible to provide reproducible scan-to-scan mode coupling as the laser scans. In OF CEAS systems and methods that are known so far, complex optical components are used for this purpose, such as Faraday isolators, variable optical attenuators, or polarization rotators. Adverse interference effects, temperature drifts and aging drifts may result from these components in the system. Achieving high stability and high reproducibility of the optical absorption measurements becomes a major problem.

In OF CEAS, one traditional configuration includes a linear V-cavity, a DFB laser coupled to the cavity though a vertex mirror, and one or more photo-detectors positioned to monitor optical powers, e.g., the intra-cavity optical power circulating within the cavity. The intra-cavity optical power buildup, while the laser is scanned over cavity modes, or free decay of the intra-cavity optical power after the laser is turned off, is defined by the cavity loss. When optical feedback is used to lock a laser to a cavity, its phase must be controlled with high precision. To provide this control, the laser-cavity optical distance must be controlled with sub-micron accuracy. Traditionally, this control is performed by placing one of the beam delivery mirrors on a piezo transducer (PZT) to control the optical path length between the laser and the cavity. Alternatively, the laser itself can be mounted on a piezo transducer. However, it is known that piezo transducers produce wobbling motion while they are expanding or contracting. This effect might cause a partial misalignment of the laser relative the cavity. Piezo transducers also tend to produce a hysteresis effect. For example, when it is desirable to change the optical path length by a specific amount (e.g., half a wavelength or a full wavelength), it can be difficult to determine how much voltage to apply relative to the previous value due to hysteresis. Moreover, the applications which use high voltage power suppliers to drive piezo transducers are restricted.

Therefore it is desirable to provide OF CEAS systems and methods that overcome the above and other problems, and in particular the problems associated with the use of piezo transducers or similar elements.

BRIEF SUMMARY

The present invention relates generally to optical spectroscopy systems and methods and more specifically to systems and methods for controlling the optical path length between a laser and cavity in optical spectroscopy systems. The optical spectroscopy systems and methods are particularly useful for measuring trace gasses.

Embodiments of the present disclosure advantageously enable control of the optical path length between a feedback enabled laser and a cavity. In certain embodiments, control of the optical feedback phase is achieved by controlling or adjusting the density of a medium along an optical path between the laser and the cavity. In the present embodiments, laser-cavity phase control is advantageously achieved without the piezo actuators or similar actuator elements present in prior systems, and more importantly without the instability or hysteresis behavior caused by such elements.

In certain embodiments, the optical distance between a laser and a cavity is varied by changing the gas pressure in the optical path between the laser and cavity. The gas pressure may be changed in the entire path or a portion of the path separating the laser and the cavity. The optical distance or path length in any media is the physical distance multiplied by the refraction index. The refraction index of a gas can be represented with high accuracy as a sum of one and a term proportional to the gas density. Changing the gas pressure in a certain volume causes a change of the gas density, which changes the refraction index of the gas medium in that volume and hence the optical path length of light traveling through the gas medium.

According to an embodiment, an optical spectroscopy system is provided that typically includes a resonant optical cavity having at least two cavity mirrors, one of which is a cavity coupling mirror, a laser that emits laser light, wherein the laser is responsive to optical feedback light emerging from the cavity, and mode matching optics configured to couple the laser light to the cavity via the cavity coupling mirror. The system also typically includes a phasor element positioned along an optical path between the laser and the cavity coupling mirror, wherein the phasor element includes a gas medium within a volume defined by the phasor element and wherein the phasor element is configured to adjust or control an optical path length of the laser light between the laser and the cavity coupling mirror by adjusting or controlling a density of the gas medium within the phasor volume. The system further typically includes a detector configured to measure an intensity of the intracavity optical power of light circulating in the cavity and to generate a signal representing the intracavity optical power of light circulating in the cavity.

According to another embodiment, a method is provided for controlling an optical path length between a laser and a resonant optical cavity, wherein the laser emits laser light and is responsive to optical feedback light emerging from the resonant optical cavity, and wherein the resonant optical cavity has at least two cavity mirrors, one of which is a cavity coupling mirror. The method typically includes coupling the laser light to the cavity via the cavity coupling mirror using mode matching optics, adjusting an optical path length between the laser and the cavity coupling mirror by adjusting a density of a gas medium between the laser and the cavity coupling mirror, and measuring an intensity of the intracavity optical power of light circulating in the cavity and generating a signal representing the intracavity optical power of light circulating in the cavity.

Reference to the remaining portions of the specification, including the drawings and claims, will realize other features and advantages of the present disclosure. Further features and advantages of the present disclosure, as well as the structure and operation of various embodiments of the present disclosure, are described in detail below with respect to the accompanying drawings. In the drawings, like reference numbers indicate identical or functionally similar elements.

BRIEF DESCRIPTION OF THE SEVERAL VIEWS OF THE DRAWING(S)

FIG. 1 illustrates an optical spectroscopy system according to one embodiment.

FIG. 2 a simulated change in the optical length as a function of the gas pressure, where the physical path length is 10 cm, and the refraction index is n=1.00027321.

DETAILED DESCRIPTION

Embodiments described herein provide for control of the optical path length between a feedback enabled laser and a cavity, and hence the optical feedback phase, by controlling or adjusting the density of a medium along an optical path between the laser and the cavity.

Figure 1:
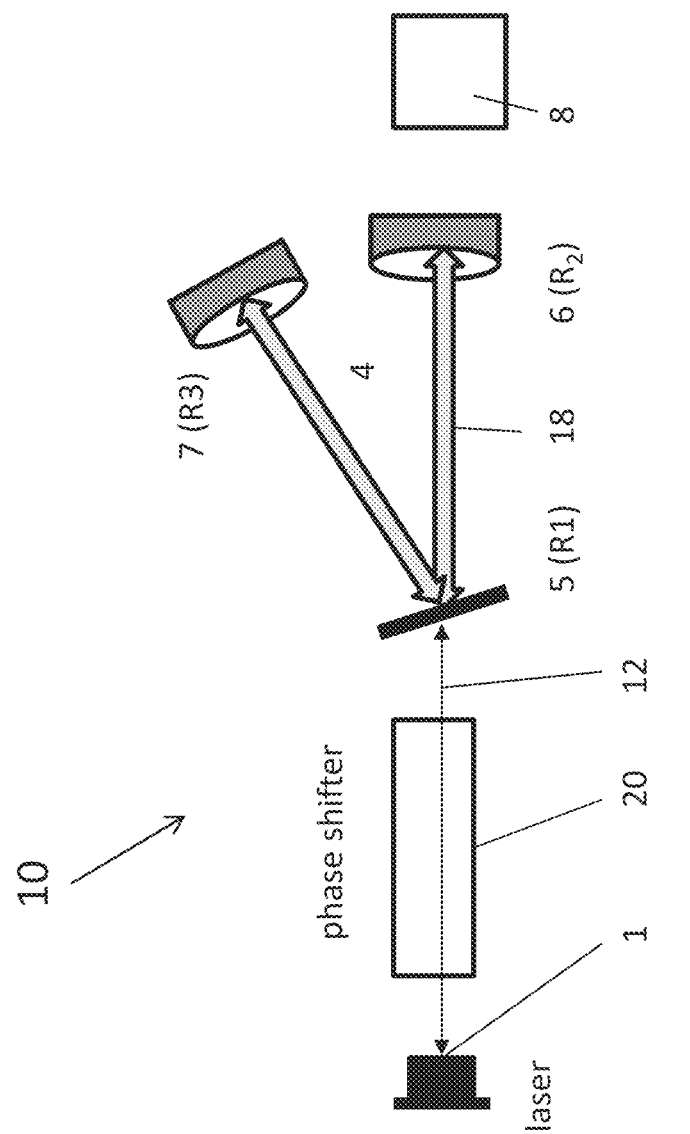

FIG. 1 illustrates an optical spectroscopy system (OSS) 10 according to one embodiment. As shown, OSS 10 includes a laser source 1 that emits coherent light, such as continuous wave laser light, an optical cavity 4 and at least one detector, detector 8, positioned to detect light emerging from the cavity. As shown, detector 8 is positioned to detect light emerging from cavity mirror 6, however, it should be appreciated that detector 8 may be position to detect light emerging from mirrors 5, 6 or 7. Additional detectors may be included as desired. Detector 8 receives or detects light emerging from cavity mirror 6 and generates a signal representing the intracavity optical power of the light circulating in the cavity.

As shown, cavity 4 is a V-shaped cavity defined by cavity coupling mirror 5 and mirrors 6 and 7. It should be appreciated that the cavity could be a linear cavity with two or more mirrors, or a ring shaped cavity with three or more mirrors, or any other structure having three or more mirrors. An enclosure or housing (not shown) provides an air tight seal for cavity 4 such as to allow control of the environment within the housing and hence the cavity 4. One or more optical components (not shown) are configured and arranged to facilitate directing laser light from source 1 to the optical cavity 4 via cavity coupling mirror 5 and to ensure the mode matching of the laser to the cavity. Such components may include, for example, one or more lens elements, one or mirror elements, and/or a beam splitting element, e.g., positioned and aligned so as to allow substantially all of the incident light emitted or generated by source 1 to impinge on cavity coupling mirror 5, and to direct (e.g., reflect or refract) a portion of the incident light beam onto a detector (not shown). Cavity coupling mirror 5, in this embodiment, is arranged at an angle with respect to beam incident along path 12, although it could be perpendicular to beam path 12. A portion of light incident along path 12 enters cavity 4 via mirror 5, and the remainder is reflected away from path 12. Depending on the frequency of the incident light and the optical length of cavity 4 (e.g., optical length from mirror 7 to mirror 5 to mirror 6) light 18 circulating in the cavity may build up and resonate at one or a plurality of cavity modes defined by the optical length of the cavity. A portion of the intra-cavity light 18 circulating in cavity 4 between mirrors 7, 5 and 6, emerges or escapes via mirror 5 and passes back to source 1 along path 12.

In certain aspects, source 1 includes a laser or other coherent light source that is sensitive or responsive to optical feedback. One useful laser is a semiconductor diode laser that is sensitive to optical feedback from light impinging on the laser and emerging from the cavity, e.g., from coupling mirror 5 along path 12 in the current configuration. In general, useful laser sources might include diode lasers, quantum cascade lasers and solid state lasers, any external cavity laser, etc. The reflectivities, R (or transmissivities, T=1−R), of mirrors 5 (R$_1$), 6 (R$_2$) and 7 (R$_3$) define the intensity of the feedback light emerging from the cavity 4 along path 12 and hence the optical feedback intensity provided to laser 1. Mirror 5 is shown as having a flat surface presented to the cavity 4, however, it should be appreciated that mirror 5 may have a concave mirror surface presented to cavity 4.

Source 1 is also preferably capable of being frequency scanned, whereby a mean optical frequency of the laser is adjustable over a range of frequencies. This can be accomplished as is well known, such as, for example, by adjusting the current applied to a diode laser and/or adjusting a temperature of the laser medium. In certain aspects, the cavity 4 is also capable of being frequency scanned, e.g., by changing or adjusting an optical length of the cavity, whereby an optical frequency of a cavity resonance peak is adjustable over a range of frequencies. Adjustment of the optical length of the cavity 4 can include adjusting or modulating a relative position of one or more of the cavity mirrors (e.g., using a piezo transducer coupled with the mirror), adjusting a pressure of the medium within cavity 4 or other ways as are known to one skilled in the art. A control subsystem (not shown) receives signals from the various detectors and sensors and generates appropriate control signals to control operation of various active components of OSS 10, including for example, the source 1, cavity PZT where present, and phasor 20 as will be discussed below in more detail.

In certain embodiments, OSS 10 is useful for detecting trace gases within a gas mixture present in the cavity 4. When the frequency of the light emitted by source 1 approaches the frequency of one of the cavity modes, the light entering the cavity 4 begins to fill the cavity to that mode. The optical intensity of the light 18 circulating inside the resonance cavity reflects total cavity loss at the moment when the frequency of the laser light coincides with the cavity mode transmission peak. The total cavity loss is a sum of the cavity mirror losses and losses caused by absorption by one or more components of the gas mixture present in the cavity. Analyte absorption, e.g., absorption losses caused by absorption by the one or more gas components, is determined based on the difference of the cavity loss when the absorbing component is present in an analyzed gas and the cavity loss when the absorbing component is absent in a reference gas.

As shown in FIG. 1, a phase shifter 20, or phasor 20, is provided to control an optical path length of light path 12. Phasor 20 advantageously enhances control of the optical feedback, and more specifically control of the phase of the optical feedback light returning to source 1 from cavity 4. Phasor 20 includes a housing structure that defines an internal volume. The internal phasor volume may be a closed volume, or it may be open to atmospheric pressure. A gas medium is present within the volume. In certain aspects, the gas medium includes air. Other gasses may be used. Phasor 20 allows for adjustment or control of the optical path length of the laser light between the laser and the cavity coupling mirror by adjusting or controlling the density of the gas medium within the phasor volume. That is, the phasor 20 allows for control of the total optical path length between the cavity and the laser source by controlling the optical path length encompassed by the phasor volume.

It should be appreciated that the phasor volume may encompass a portion of the path 12 along which laser light and feedback light travels as shown or it may encompass the entire path length 12. For example, as shown, a housing structure defining the phasor volume is positioned between the laser and the cavity along path length 12. In this embodiment, the housing structure includes optically window elements at either end of the structure to allow light to pass through the phasor volume. Alternatively, the housing structure may include, or hold, one of the cavity coupling mirror 5 or the source 1. In this case, the opposite end of the housing structure includes an optical window element that allows light to pass. Alternatively, the phasor volume may encompass the entire path length 12 between the laser 1 and the cavity coupling mirror 5. For example, the housing structure defining the phasor volume may be coupled to, and hold, both cavity coupling mirror 5 and source 1.

The refractive index, n, of a gas can be represented with high accuracy as a sum of one (1) and a term proportional to the gas density. Changing the gas density in the cavity thus causes a change in the optical path length in the cavity. Because the gas density is proportional to the gas pressure and inversely proportional to the gas absolute temperature, the index of refraction of a gas minus 1, n−1, is similarly proportional to the gas pressure and inversely proportional to the absolute gas temperature. See, e.g., Owens, James C., "Optical Refraction Index of Air: Dependence on Pressure, Temperature and Composition," Applied Optics, pp. 51-59, Vol. 6, No. 1, January 1967, which is hereby incorporated by reference.

Figure 2:
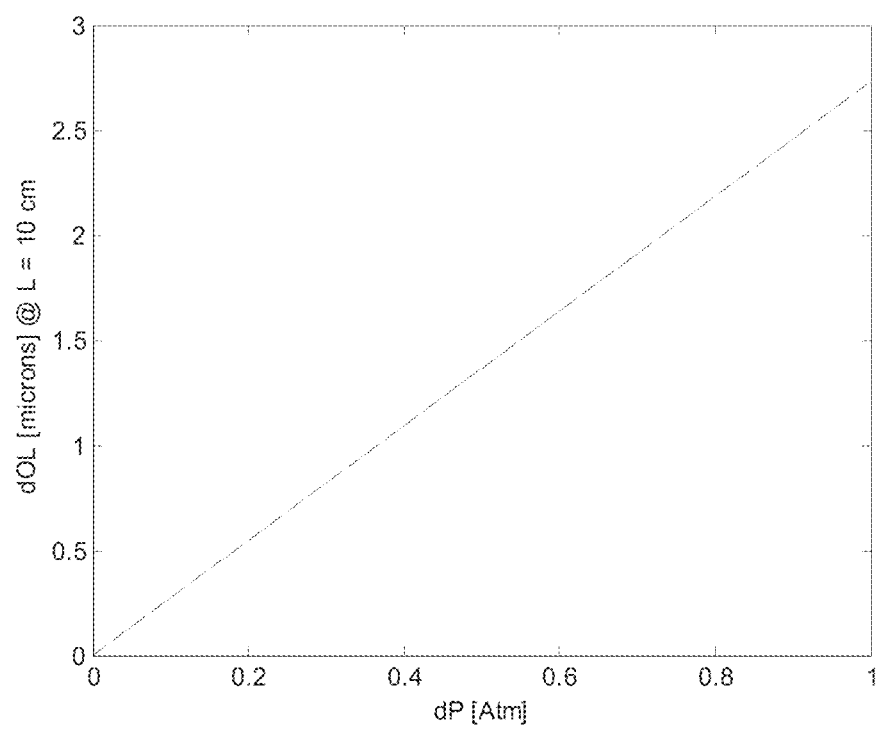

At fixed temperature, the optical length, OL, in a gas media can be represented as $OL=L \times (1+kP)$, where L is the physical length, P is the gas pressure, and k is a coefficient. For air at 25° C., $k=2.73E-4$ $Atm^{-1}$. The changing of the optical length $\Delta OL$ can be represented as $\Delta OL=L \times k(P-P_0)$. FIG. 2 shows a simulated change in the optical length as a function of the gas pressure, where the physical path length is 10 cm, and the refraction index is n=1.00027321.

Figure 3:
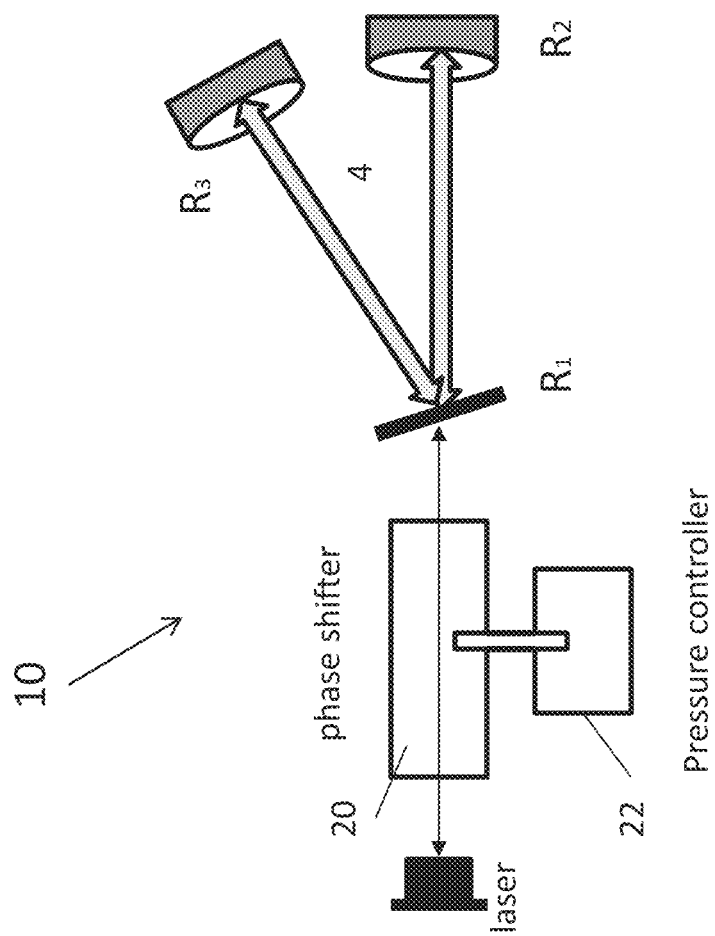
FIG. 3 illustrates a phasor with a pressure control element in fluid communication with the phasor volume according to an embodiment.

In the embodiment shown in FIG. 3, phasor 20 includes a pressure control element 22, or pressure controller 22, in fluid communication with the phasor volume. The pressure controller 22 may include a negative (i.e., vacuum) or positive pressure pump. In response to control signals received from the control subsystem (not shown), the pressure controller adjusts the gas pressure in the phasor volume. In this embodiment shown in FIG. 3, the phasor volume is closed, or fixed. Hence, adjusting the pressure of the closed volume will adjust the density of the gas medium within the closed volume. Increasing the pressure adds more gas molecules to the closed volume and therefore increases the density of the gas medium, and decreasing the pressure reduces the number of gas molecules and therefore reduces the density.

Figure 4:
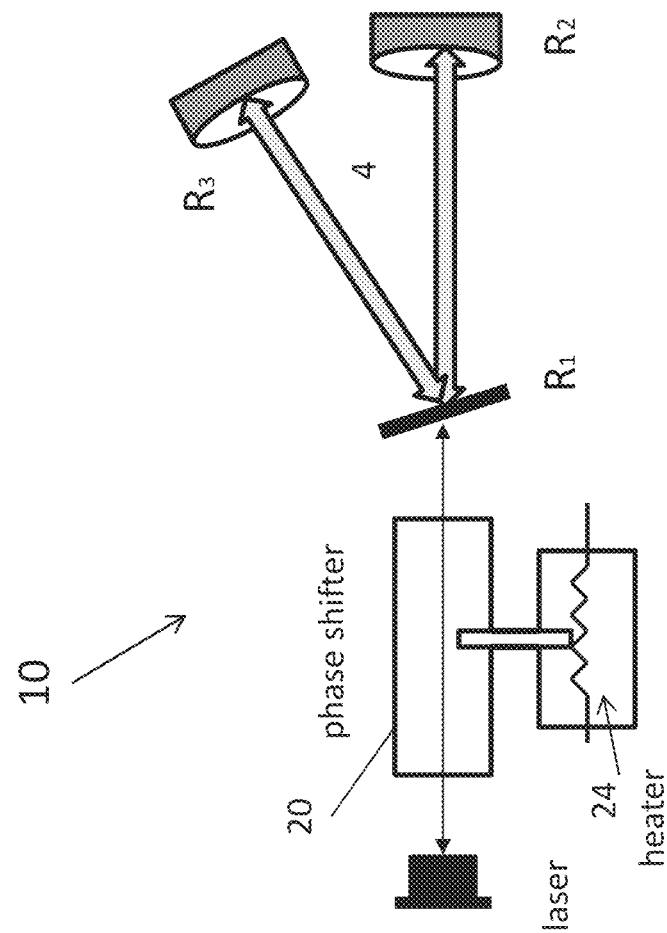
FIG. 4 illustrates a phasor with a temperature control element in a chamber in fluid communication with the phasor volume according to an embodiment.

In the embodiment shown in FIG. 4, phasor 20 includes a temperature control element 24, or temperature controller 24, in a chamber in fluid communication with the phasor volume. The temperature controller 24 may include one or more elements, such as one or more resistive elements, which heats up when a current is applied thereto as is well known. Other devices such as heat pumps, etc. to increase or decrease the temperature may be used. In response to control signals received from the control subsystem (not shown), the temperature controller adjusts the temperature of the chamber volume. In this embodiment shown in FIG. 4, the total volume (chamber volume and phasor volume) is closed, or fixed. Hence, adjusting the temperature of the chamber volume will similarly adjust the pressure of the gas medium in both the phasor volume and the chamber volume and hence the density of the gas medium within the phasor volume. Increasing the temperature in the chamber volume increases the density in the phasor volume, and decreasing the temperature reduces the density in the phasor volume.

Figure 5:
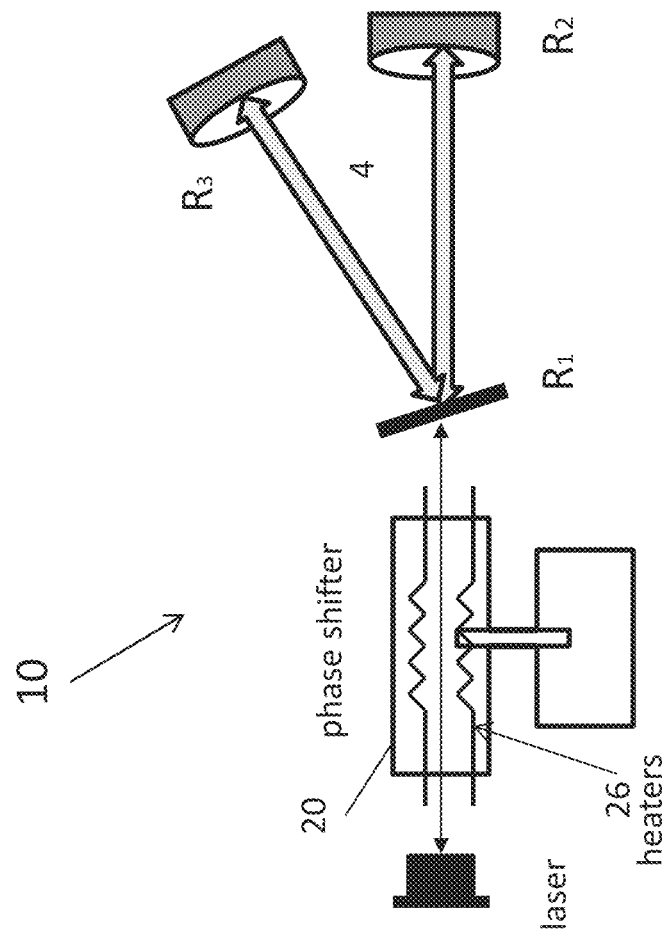
FIG. 5 illustrates a phasor having a temperature control element within the phasor volume according to an embodiment.

In the embodiment shown in FIG. 5, phasor 20 includes a temperature control element 26, or temperature controller 26, within the phasor volume. The temperature controller 26 may include one or more elements, such as one or more resistive elements. Other devices such as heat pumps, etc. to increase or decrease the temperature may be used. In response to control signals received from the control subsystem (not shown), the temperature controller adjusts the temperature of the phasor volume. In this embodiment shown in FIG. 5, the total volume (chamber volume and phasor volume) is closed, or fixed. Hence, adjusting the temperature of the phasor volume will similarly adjust the pressure of the gas medium in both the phasor volume and the chamber volume and hence the density of the gas medium within the phasor volume. Increasing the temperature in the phasor volume decreases the gas density in the phasor volume, and decreasing the temperature increases the gas density in the phasor volume. It should be appreciated that in this configuration, redistribution of the gas density is occurring as the pressure is the same in both volumes, but the temperatures in the phasor volume and the chamber volume are different.

Figure 6:
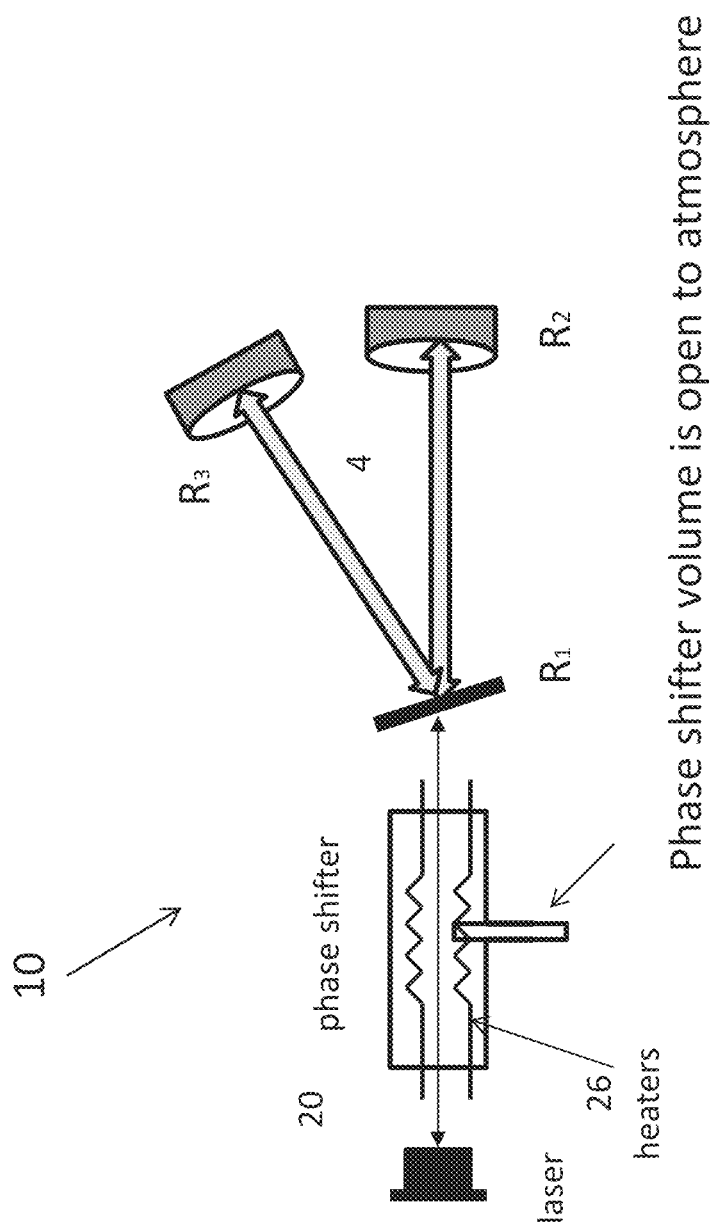
FIG. 6 illustrates a phasor having a temperature control element within the phasor volume wherein the phasor volume is open to ambient conditions according to an embodiment.

Similar to the embodiment shown in FIG. 5, phasor 20 in FIG. 6 includes a temperature control element 26, or temperature controller 26, within the phasor volume. However, in FIG. 6, the phasor volume is open to the atmosphere and is therefore at substantially constant pressure (according to the timescale of fluctuations of the atmospheric pressure). The temperature controller 26 may include a resistive element, which heats up when a current is applied thereto as is well known. Other devices such as heat pumps, inductive elements, etc. to increase or decrease the temperature may be used. In response to control signals received from the control subsystem (not shown), the temperature controller adjusts the temperature of the phasor volume. Hence, adjusting the temperature with the constant pressure will adjust the density of the gas medium and hence the refractive index of the gas medium within the open volume. Increasing the temperature in the open-to-atmosphere volume decreases the density of the gas medium in the phasor volume, and decreasing the temperature increases the density.

Figure 7:
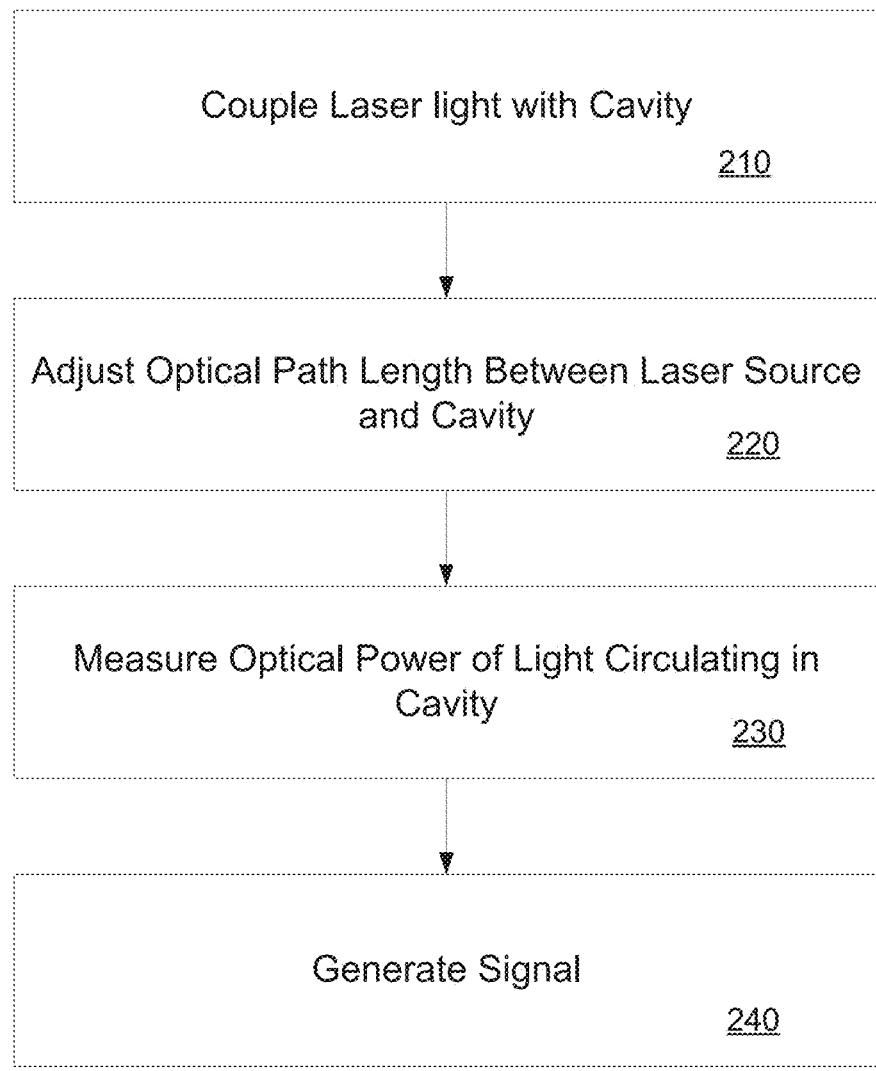
FIG. 7 illustrates a method of controlling an optical path length according to an embodiment.

FIG. 7 illustrates a method 200 of controlling an optical path length according to an embodiment. In step 210, laser light from a laser source is coupled to a resonant optical cavity via a cavity coupling mirror, e.g., using mode matching optical elements. In step 220, an optical path length between the laser source and a cavity coupling mirror is adjusted. For example, in certain aspects, the optical path length is adjusted by adjusting a density of a gas medium between the laser source and the cavity coupling mirror. The gas medium may be contained within a volume defined by a structural housing, e.g., the structural housing defining the volume of phasor 20. The phasor volume may be closed, or it may be open. In step 230, a measurement of the optical power of light circulating in the resonant optical cavity is made, for example, measuring a ring-down event after the laser is shut off, or the laser light is otherwise shuttered from reaching the cavity, or measuring continuously as one or more cavity resonance modes are "locked" by the laser source. A signal representing the detected/measured intracavity optical power of light may be generated in step 240. The generated signal may be used to determine parameters of the system, such as an absorbance value of one or more gas components in the resonant optical cavity.

Additional aspects of OF-CEAS systems can be found in US Patent Application Publication 2013/0050706 A1 (corresponding to application Ser. No. 13/218,359) and US Patent Application Publication 2013/0083328 A1 (corresponding to application Ser. No. 13/252,915), which are each incorporated herein by reference for all purposes.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the embodiments (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All method or process steps described herein can be performed in any suitable order unless otherwise indicated herein or otherwise clearly contradicted by context. The use of any and all examples, or exemplary language (e.g., "such as") provided herein, is intended merely to better illuminate the various embodiments and does not pose a limitation on the scope of the various embodiments unless otherwise claimed. No language in the specification should be construed as indicating any non-claimed element as essential to the practice of the various embodiments. Exemplary embodiments are described herein, including the best mode known to the inventors. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, all modifications and equivalents of the subject matter recited in the claims appended hereto are included as permitted by applicable law. Moreover, any combination of the above-described elements in all possible variations thereof is encompassed unless otherwise indicated herein or otherwise clearly contradicted by context.

The invention claimed is:

1. An optical spectroscopy system comprising:
a resonant optical cavity having at least two cavity mirrors, one of which is a cavity coupling mirror;
a laser that emits laser light;
a phasor element positioned along an optical path between the laser and the cavity coupling mirror, wherein the phasor element includes a gas medium within a volume defined by the phasor element and wherein the phasor element is configured to adjust or control an optical path length of the laser light within the volume by adjusting or controlling a density of the gas medium within the volume; and
a detector configured to measure an intensity of light emerging from one of the at least two cavity mirrors other than the cavity coupling mirror and to generate a signal representing an intracavity optical power of light circulating in the cavity.

2. The system of claim 1, wherein the laser emits continuous wave laser light, and wherein the laser is capable of being scanned whereby a mean optical frequency of the laser is adjustable over a range of frequencies.

3. The system of claim 2, further including a means for adjusting the mean optical frequency of the laser so as to scan the mean optical frequency of the laser over at least one cavity resonance peak.

4. The system of claim 1, wherein the cavity has a configuration selected from the group consisting of a ring cavity having three or more cavity mirrors, a linear cavity having two or more cavity mirrors, and a V-shaped cavity having three cavity mirrors.

5. The system of claim 1, wherein the volume is a closed volume.

6. The system of claim 1, wherein the volume is open to ambient air pressure.

7. The system of claim 1, wherein the phasor element includes a pressure control element in fluid communication with the volume.

8. The system of claim 1, wherein the pressure control element includes one of a positive pressure pump or a negative pressure pump.

9. The system of claim 1, wherein the phasor element includes one or more heating elements within the volume, wherein the one or more heating elements heat the volume and thereby adjust the density of the volume.

10. The system of claim 1, wherein the phasor volume encompasses the entire optical path between the laser and the cavity coupling mirror.

11. The system of claim 1, wherein the laser is a diode laser and wherein the laser is responsive to optical feedback light emerging from the cavity coupling mirror and impinging on the laser along an optical path between the laser and the cavity coupling mirror.

12. The system of claim 1, wherein the phasor volume encompasses a portion of the optical path between the laser and the cavity coupling mirror.

13. A method for controlling an optical path length between a laser and a resonant optical cavity, wherein the laser emits laser light and is responsive to optical feedback light emerging from the resonant optical cavity, the resonant optical cavity having at least two cavity mirrors, one of which is a cavity coupling mirror, the method comprising:
coupling the laser light to the cavity via the cavity coupling mirror;
adjusting an optical path length between the laser and the cavity coupling mirror by adjusting a density of a gas medium between the laser and the cavity coupling mirror; and
measuring an intensity of light emerging from one of the at least two cavity mirrors other than the cavity coupling mirror and generating a signal representing an intracavity optical power of light circulating in the cavity.

14. The method of claim 13, wherein the gas medium is contained within a volume defined by a phasor element positioned between the laser and the cavity coupling mirror.

15. The method of claim 14, wherein the phasor volume encompasses a portion of the optical path between the laser and the cavity coupling mirror.

16. The method of claim 14, wherein the phasor element includes a pressure control element in fluid communication with the volume, and wherein adjusting the optical path length includes adjusting a pressure of the gas medium within the volume to thereby adjust the density of the gas medium.

17. The method of claim 16, wherein the pressure control element includes a pump in fluid communication with the volume, and wherein adjusting the pressure of the gas medium within the volume includes applying one of a negative pressure or a positive pressure using the pump.

18. The method of claim 16, wherein the pressure control element includes one or more heating elements, and wherein adjusting the optical path length includes heating the volume with the one or more heating elements to thereby adjust the density of the gas medium within the volume.

19. The method of claim 14, wherein the gas medium encompasses the entire optical path between the laser and the cavity coupling mirror.

20. The method of claim 13, further including adjusting a mean optical frequency of the laser so as to scan the mean optical frequency of the laser over one or more modes of the optical resonance cavity that have a frequency within a range of frequencies of the laser.

* * * * *